United States Patent [19]

Nakajima et al.

[11] Patent Number: 4,767,791
[45] Date of Patent: Aug. 30, 1988

[54] PROCESS FOR SYNTHESIZING METHANOL WITH AN OPTIMAL TEMPERATURE PROFILE USING A CONCENTRIC PIPE REACTOR

[75] Inventors: Yoshimitsu Nakajima; Kensuke Niwa; Kazuhiro Morita, all of Tokyo; Hiroshi Makihara, Hiroshima, all of Japan

[73] Assignee: Mitsubishi Jukogyo Kabushiki Kaisha, Japan

[21] Appl. No.: 928,665

[22] Filed: Nov. 6, 1986

Related U.S. Application Data

[62] Continuation of Ser. No. 670,339, Nov. 9, 1984, abandoned.

[30] Foreign Application Priority Data

Nov. 14, 1983 [JP] Japan ............... 58-213724

[51] Int. Cl.[4] .................................. C07C 27/06
[52] U.S. Cl. ............................ 518/712; 422/197; 422/203
[58] Field of Search ............... 422/196–198, 422/202, 203, 312; 423/659; 518/712

[56] References Cited

U.S. PATENT DOCUMENTS

| | | | |
|---|---|---|---|
| 688,020 | 12/1901 | Knietsch | 422/202 |
| 1,812,341 | 6/1931 | Jaeger | 422/202 |
| 1,826,548 | 10/1931 | Jaeger | 422/202 |
| 1,900,715 | 3/1933 | Jaeger | 422/197 |
| 4,430,304 | 2/1984 | Spurrier et al. | 422/202 |

FOREIGN PATENT DOCUMENTS

| | | |
|---|---|---|
| 149640 | 1/1980 | Japan . |
| 38568 | 3/1982 | Japan . |
| 53420 | 4/1982 | Japan . |
| 83642 | 2/1983 | Japan . |

Primary Examiner—Benoit Castel
Attorney, Agent, or Firm—McGlew and Tuttle

[57] ABSTRACT

A process for synthesizing material uses an exothermic reactor which comprises a coolant shell, two concentric pipes provided within the shell, a catalyst bed packed between inner and outer ones of the concentric pipes, an introduction tube connected to the inner pipe through which a starting fluid is introduced, and a communication path enabling the fluid after the passage of the inner pipe to be passed through the catalyst bed in a direction opposite to the direction of the passage through the inner pipe, the coolant shell having an inlet and an outlet for a coolant arranged in such a way that the flow of the coolant is parallel to the flow of the fluid within the catalyst bed. The coolant on the outside and the starting fluid on the inside of the catalyst bed cools the bed in such a way as to produce a temperature distribution along the bed that follows a maximum reaction rate line (M in FIG. 1) relating the concentration of the methanol to the temperature of the starting fluid.

2 Claims, 3 Drawing Sheets

PROCESS FOR SYNTHESIZING METHANOL WITH AN OPTIMAL TEMPERATURE PROFILE USING A CONCENTRIC PIPE REACTOR

The present invention is a continuation of application Ser. No. 670,339, filed Nov. 9, 1984, now abandoned.

BACKGROUND OF THE INVENTION

1. Field of the Invention

This invention relates to concentric pipe exothermic reactors in which exothermic reactions are carried out on solid catalysts.

2. Description of the Prior Art

In the production of ammonia, methanol and the like by vapor phase reactions performed on solid catalysts, various types of reactors have been heretofore proposed and reduced into practice in order to cool the catalyst layer or bed and properly control the distribution of temperature within the catalyst layer. Various methods have also been proposed in which not only the catalyst layer is merely cooled, but also heat of the reaction is transferred to cooling media and effectively utilized.

In continuous reactors for carrying out exothermic reactions, it is ordinary that in the vicinity of an outlet of the catalyst bed where the reaction proceeds, a concentration of reaction product becomes higher and the reaction comes closer to an equilibrium than in the vicinity of the inlet, with a lowering of the reaction rate. In the neighbourhood of the outlet of the catalyst bed, therefore, it is favorable to lower the reaction temperature, to permit the reaction system to be kept away from the equilibrium of the reaction, and to prevent the lowering of the reaction rate. At a portion near the inlet of the catalyst bed where a concentration of reaction product is sufficiently low, the system is known to be far from the equilibrium state of the reaction, so that higher temperatures are preferred.

Thus, when exothermic reactions are carried out, it is the most favorable to lower the temperature of the catalyst bed as the reaction proceeds.

FIG. 1 shows the relation between concentration of a reaction product (mol%) and reaction gas temperature, in which curve N indicates an equilibrium line for the reaction. The region at the right and upper side of the curve N is a region which cannot thermodynamically exist. Curve M is a line indicating a maximum reaction rate, showing the course of maximizing the reaction rate. In general, the maximum reaction rate line M is approximately parallel to the equilibrium line N. When the temperature distribution within the catalyst bed or the temperature distribution during the course of the reaction ideally moves on or along the curve M, the amount of catalyst required to obtain an intended reaction product becomes minimal.

In known tubular reactors such as described, for example, in Japanese Patent Publication No. 57-38568 which are cooled only by boiling water, the temperature of boiling water which is a cooling medium is approximately uniform throughout the reactor, with the problem that the temperature distribution of the catalyst bed becomes approximately uniform.

In order to improve the conditions of a reaction equilibrium, there has been proposed in Japanese Laid-open Patent Application No. 57-53420 a reactor in which in order to lower the temperature at a portion near the outlet of catalyst bed, supercooled water is fed to the portion near the outlet. In this case, the feed of supercooled water ensures the lowering of the temperature at or near the outlet of the catalyst bed. Because the transmission of heat from the supercooled water depends only on the heat transmission by convection, the cooling effect is much more reduced than the effect produced by the transmission of heat by boiling of water. This is industrially disadvantageous in leading to an increase of a required cooling area. If, on the contrary, the flow rate of cooling water is raised in order to suppress the reduction of the cooling effect, an increased pressure loss of the fluid is entailed, leading to the problem that a power requirement for pumping the water increases.

Because of the recent development of copper catalysts for the methanol synthetic reaction, catalysts which have very high activity even at low temperatures have been industrially produced. However, use of highly active catalysts results in a large quantity of heat of generation per unit amount of catalyst, requiring a larger cooling area and a more effective cooling technique. Especially, when copper catalysts used for the synthetic reaction of methanol are employed at temperatures over 300° C. over a long period, their activity deteriorates, so that a sharp temperature rise within the catalyst bed is unfavorable not only from the standpoint of choice of material for the reactor, but also from the standpoint of deterioration of the catalysts. In known tubular reactors in which boiling liquid is used for cooling, e.g. reactors described in Japanese Patent Publication No. 57-38568, when the boiling liquid is passed countercurrently with a reaction gas passed through the catalyst bed, a proportion by volume of a gas phase in the boiling liquid becomes highest in the vicinity of the inlet of the catalyst bed where the highest cooling effect is required, making the worst efficiency for heat transmission, with an attendant problem that a very sharp temperature rise takes place in the vicinity of the inlet of the catalyst bed.

Starting gases being fed into the catalyst bed should be preheated to a temperature level sufficient to allow the reaction to proceed in the catalyst bed. For instance, with copper catalysts used for the synthetic reaction of methanol, the starting gases should be preheated to over 150° C. In general, sensible heat of the hot gas from the outlet of the catalyst bed is used for preheating the starting feed gases. These gases are preheated in the heat exchanger located downstream of a reactor. The temperature of the gas at the outlet of a reactor, i.e. a gas at the outlet of the catalyst bed, is generally over 200° C. when the reactor is for synthesis of methanol. The sensible heat of the reactor outlet gas having such a high temperature level may be used not only for the preheating of starting feed gases, but also for heat recovery such as preheating of boiler feed as described in Japanese Laid-open Patent Application No. 58-83642. In the method described in the above Japanese Laid-open Patent Application, heat recovery at such a high temperature level essentially requires a heat recovery apparatus arranged parallel to a preheater for the starting feed gas with limited ranges in amount of heat being recovered in the respective apparatus.

SUMMARY OF THE INVENTION

The present invention provides a concentric pipe exothermic reactor which solves the problems involved in the prior art apparatus or methods. The concentric pipe exothermic reactor according to the present invention comprises a coolant shell, two concentric pipes provided within the shell, a catalyst bed packed between inner and outer ones of the concentric pipes, an introduction tube connected to the inner pipe through which a starting fluid is introduced, and communication means enabling the fluid, after it has passed through the inner pipe, to be passed through the catalyst bed that is between the inner and outer pipes, in a direction opposite to the direction of the passage through the inner pipe, the coolant shell having an inlet and an outlet for a coolant arranged in such a way that the flow of the coolant is parallel to the flow of the fluid within said catalyst bed.

The reactor of the present invention is so arranged as described above, by which the catalyst bed is cooled not only from the inner side of the inner pipe, but also from the outer side of the outer pipe. Thus, it is possible to make such a temperature distribution that a temperature at or near the outlet of the catalyst bed is lower than a temperature at or near the inlet. A starting fluid, e.g. a starting feed gas, which is introduced into the inner pipe whose temperature is lower than the inlet temperature of the catalyst bed can be preheated to the inlet temperature of the catalyst bed by application of part of the heat of the reaction in the catalyst bed. When the coolant passed over the outer pipe of the concentric pipe assembly is passed parallel to the flow of the reaction gas in the catalyst bed, a portion at or near the inlet of the catalyst bed in which the reaction temperature becomes the highest can be effectively cooled, enabling one to recover most of the heat of reaction as a latent heat for evaporation of the coolant.

DETAILED DESCRIPTION OF THE INVENTION

Figure 2:
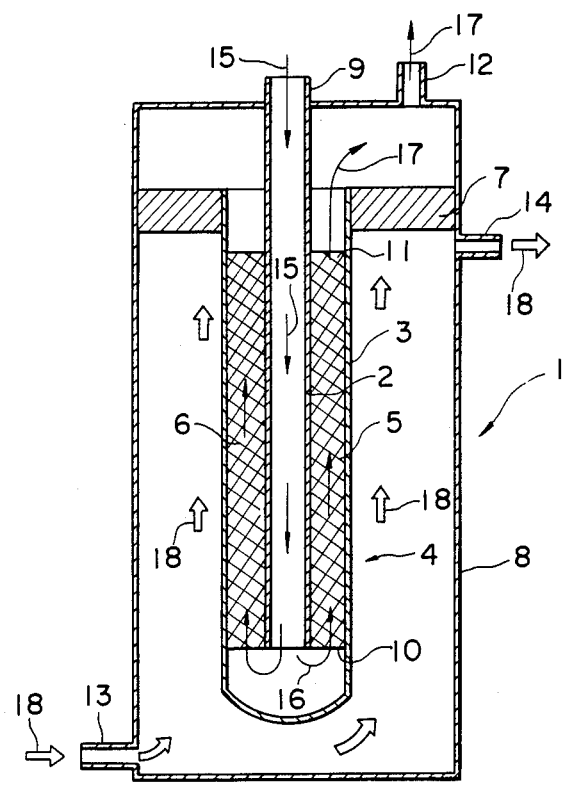
FIG. 2 is an illustrative view of a fundamental embodiment of a reactor according to the invention.

Referring now to the accompanying drawings and particularly to FIG. 2, there is shown a fundamental arrangement of a concentric pipe exothermic reactor according to the invention. The concentric pipe exothermic reactor 1 has two concentric pipes which together form an assembly generally designated 4, consisting of an inner pipe or tube 2 and an outer tube or pipe 3. In a circular or annular space 5 established between the inner and outer tubes 2, 3 is formed a catalyst bed 6 in which a catalyst is packed. The concentric pipe assembly 4 is fixed to a circular closing plate 7 through the outer tube 3 and is provided within a coolant shell 8. Outer tube 3 has a bottom that is closed by a bottom plate 3' forming sealing means for closing and communicating the lower ends of the inner and outer tubes 2,3, together.

The inner tube 2 has an inlet 9 at one end thereof which communicates with outside of the reactor 1 and communicates at the other end thereof with one end of the circular space 5, i.e. an inlet 10 of the catalyst bed 6, at the end of the concentric pipe assembly 4. The other end of the circular space 5 or an outlet 11 of the catalyst bed 6 is associated with a reaction gas outlet 12 communicated to outside of the reactor 1. The catalyst bed 6 is held up in space 5 by a perforated plate or the like, at inlet 10. This holds the bed above bottom plate 3'.

The coolant shell 8 has an inlet 13 for coolant at a lower side near the inlet 10 of the catalyst bed and an outlet 14 for coolant at a side near the outlet 11 of the catalyst bed. During the time when a starting gas or fluid feed 15 is introduced from the inner tube inlet 9 of the assembly 4 (corresponding to A point of FIG. 1) and arrives at the lower end of the assembly 4, i.e. the catalyst bed inlet 10, (corresponding to B point of FIG. 1), it is preheated to a level of B point of FIG. 1 by means of heat of reaction generated in the circular catalyst bed 6. The preheated inlet gas 16 is fed into the circular catalyst bed 6. While the inlet gas 16 is passed through the circular catalyst bed 16 (along the curve B—B'—C of FIG. 1), the reaction proceeds and the gas is discharged as an outlet gas or product fluid 17 which is a reaction product gas.

In the vicinity of the inlet 10 of the catalyst bed, it is general that an amount of heat of reaction per unit amount of the catalyst is great, so that there exists a portion (corresponding to B' point of FIG. 1), near the inlet 10 of the catalyst bed whose temperature is higher than the temperature at the inlet 10 (corresponding to B point) of the catalyst bed. In the reactor of the present invention, however, the temperature of the starting gas feed 15 serving as a cooling medium and passed through the inner tube 2 is lower at the side of the outlet 11 than at the side of the inlet 10 of the catalyst bed 6. As a result, the catalyst bed 6 is cooled with the starting gas 15, so that the temperature distribution of the catalyst bed 6 is so controlled as to be lower in the vicinity of the outlet than in the vicinity of the inlet as in the curve B—B'—C shown in FIG. 1. More particularly, the reactor of the present invention is cooled from the outside of the outer tube 3 of the concentric pipe assembly 4 by means of a coolant 18 which is boiled, i.e. the heat transmission by boiling is mainly utilized. The lowering of the temperature in the vicinity of the outlet 11 of the catalyst bed 6 is realized by cooling with the starting feed gas 15 passed parallel to the stream of the gas in the catalyst bed 6. In the practice of the invention, not only the coolant 18 serves as the cooling medium, but also the starting feed gas 15 acts as another cooling medium. The temperature distribution in the catalyst bed 6 is thus as shown in the curve B—C of FIG. 1, enabling one to realize the reaction procedure along the maximum reaction rate curve M.

The above effects can be enhanced at low cost by providing fins or grooves at part or entirety of the inside of the inner tube 2 in order to facilitate the transmission of heat.

In the reactor 1 of the invention, a cooling area can be increased by adoption of the assembly 4. In addition, the inner tube 2 which is one of the cooling surfaces is designed to have a pressure difference between the inner and outer wall surfaces, which is at most approximately equal to the pressure loss of the reaction gas in the circular catalyst bed 6. Thus, no specific design for pressure resistance is needed in the practice of the invention.

In the reactor 1 of the invention, the stream of the coolant 18 is designed to be parallel to the direction of the reaction gas flow passed through the catalyst bed. In the vicinity of the inlet 10 of the catalyst bed, heat of generation per unit amount of the catalyst is greater than in the vicinity of the outlet 11, with the result that heat of generation per unit cooling area becomes great in the case of pipe reactors such as the reactor 1 of the present invention. As particularly shown in FIG. 1, the high temperature point B' exists in the vicinity of the inlet 10.

Figure 1:
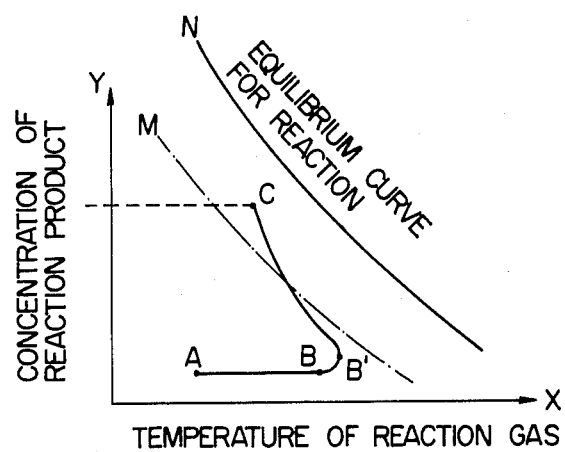
FIG. 1 is a graph showing the relation between reaction gas temperature and concentration of a reaction product obtained in exothermic reaction.

When the coolant 18, as boiled, is used for cooling, the boiling coolant evaporates by heat transmission to form a stream of a gas-liquid mixed phase with an increasing ratio by volume of the gas phase to the liquid phase. When the ratio increases, the efficiency of heat transmission (coefficient of heat transmission) decreases. In the reactor of the present invention, the inlet 10 of the catalyst bed corresponds to a side upstream of the boiling liquid serving as the coolant 18 and is thus the highest in efficiency of heat transmission. Accordingly, the temperature of point B' where the temperature rise occurs in the vicinity of the inlet 10 of the catalyst bed as shown in FIG. 1 can be suppressed to be low.

The reactor 1 of the present invention is so designed that preheating of the starting feed gas is effected in the concentric pipe assembly within the reactor. It is not necessary to divide, as described in Japanese Laid-open Patent Application No. 58-83642, the sensible heat of a high temperature level involved in the reactor outlet gas and all heat can be effectively recovered by suitable means.

Figure 3:
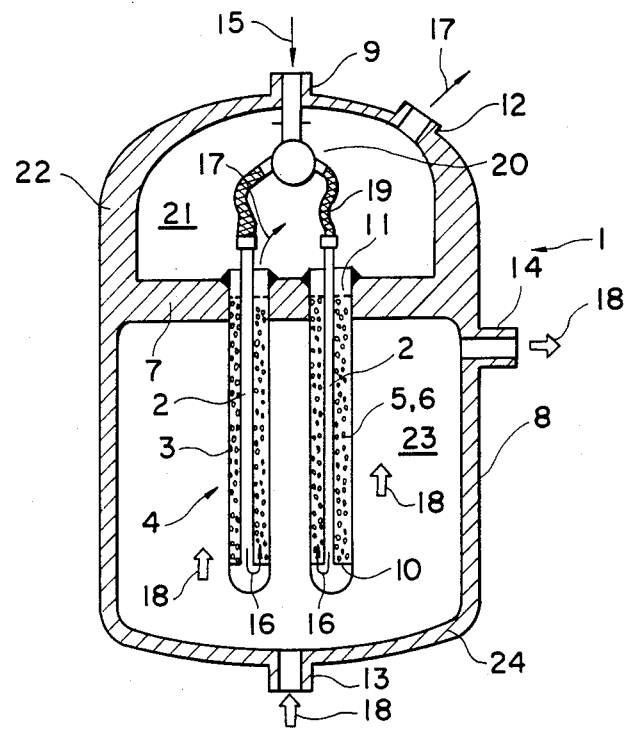
FIGS. 3 through 5 are, respectively, longitudinal sectional views of concentric pipe reactors according to other embodiments of the present invention.

FIG. 3 shows another embodiment according to the present invention. Reference numerals 1 through 18 designate similar parts or means as described with reference to FIG. 2. In FIG. 3, indicated at 19 are flexible tubes, at 20 is a inlet header for starting feed gas, at 21 is a channel in which the reaction gas is collected and passed, at 22 is a mirror plate at the side of the channel 21 for the reaction gas, at 23 is a space through which the boiling liquid 18 serving as a coolant flows, and at 24 is a mirror plate at the side of the boiling liquid.

The starting gas feed 15 is introduced into the inlet header 20, after which it is passed through the respective flexible tubes into the inner tube 2 of each concentric pipe assembly 4. The gas passed through the inner tubes 2 is preheated to a predetermined temperature before reaching the lower ends 10 of the concentric pipes. The thus preheated gas is passed into the circular catalyst bed 6 established between the outer and inner tubes 3, 2 of each pipe where the reaction starts. After completion of the reaction, the resulting gas is collected in the channel 21 and delivered as a reaction product gas 17 to outside of the reactor 1.

On the other hand, the boiling liquid which is a coolant is introduced from the inlet 13 into the space 23 surrounded by the shell 8, in which it is partly evaporated while cooling the outer tubes 3 and passed through the outlet 14 to outside.

In this embodiment, the mirror plate 22 of the channel 21 and the circular plate 7 are provided to constitute a pressure chamber at the gas feed side, in which a non-pressure container comprising the inlet header 20 and the flexible tubes 19 is accomodated in the chamber. At the side where the boiling liquid exists there is a pressure chamber composed of the shell 8 and the mirror plate 24.

Figure 4:
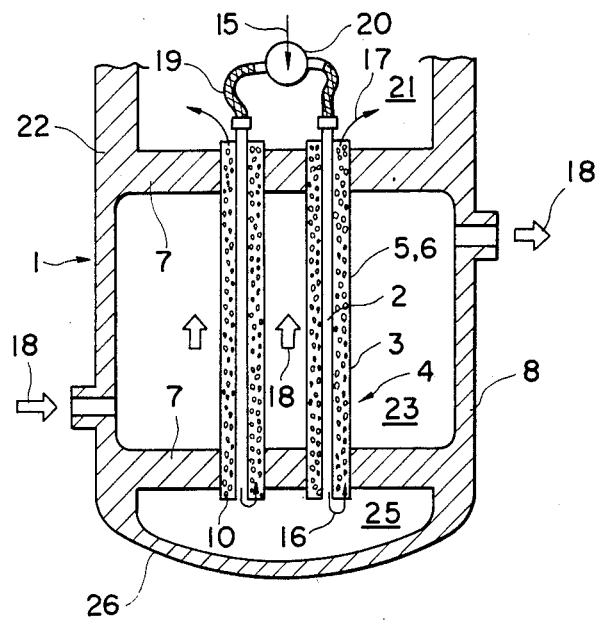

FIG. 4 shows a further embodiment of the present invention, in which reference numerals 1 through 23 indicate similar parts or means as shown in FIGS. 2 and 3. In FIG. 4, indicated at 25 is a channel portion in which the starting gas feed 15 is collected and then passed and at 26 is a mirror plate provided at the side of the channel portion 25 in which the starting feed gas 15 is collected and flows. The flow paths of the respective fluids are similar to those of FIG. 3. The reactor 1 of this embodiment has upper and lower circular plates 7, by which the starting gas feed 15 preheated by passage through the inner tubes 2 is collected in the channel portion 25 at the lower end portion 10 of the concentric pipes and introduced into the circular catalyst bed 6.

Figure 5:
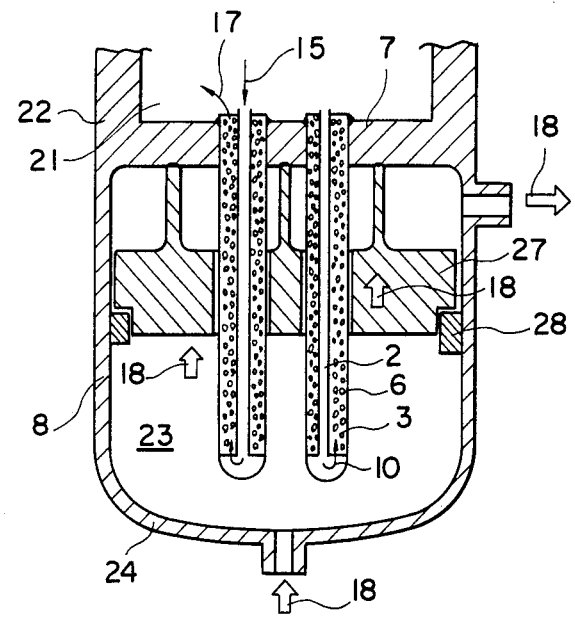

FIG. 5 shows a still further embodiment according to the present invention, in which reference numerals 1 through 24 indicate similar parts or means as in the foregoing figures. In FIG. 5, indicated at 27 is a support for the circular plate 7 and the support constitutes a simply supported beam in the form of parallel or lattice plates. Indicated by 28 is a support ring which is provided along the inner circumference of the shell 8 and supports the circular plate support 27. Although the flow paths of the respective fluids are the same as in the case of FIG. 3, the circular plate 7 of the reactor 1 in this embodiment is supported with the support 27 which serves to mitigate the stress exerted on the circular plate 7 while supporting the plate 7 from axial directions of the reactor 1. The support 27 is in turn supported with the support ring 28 fixed to the shell 8. This support arrangement is very advantageous especially when the reactor 1 is designed to be large in size.

Figure 6:
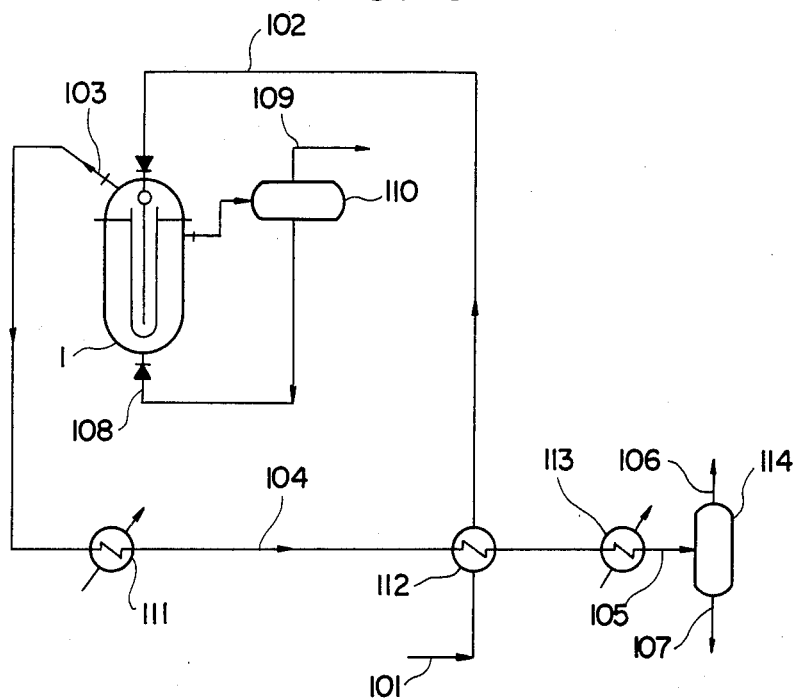
FIG. 6 is a block diagram of a plant using a reactor according to the invention.

FIG. 6 is an example of a process using the reactors according to the present invention.

Indicated at 1 is a concentric pipe exothermic reactor according to the invention, at 101 is a starting gas feed, at 102 is a partially preheated starting gas feed, at 103 is a reaction product gas, at 105 is a partially cooled and partly condensed reaction product gas, at 106 is a recycle gas from which the condensed product has been separated, at 107 is the condensed product, at 108 is a boiling liquid being fed to the reactor as a coolant, at 109 is steam generated in the reactor, at 110 is a gas-liquid separator for boiling water, at 111 is a heat exchanger for heat recovery, at 112 is a preheater for the starting gas feed, at 113 is a condenser for condensing the reaction product gas, and at 114 is a separator for separating the condensed product.

In operation, the starting gas feed 101 is partly preheated in the preheater 112 and passed into the reactor 1, from which the reaction product gas 103 is withdrawn. After heat recovery in the heat exchanger 111, the the gas 103 is again fed into the preheater 112 wherein it is cooled. The product is further partly condensed in the condenser 113 and is separated in the separator into the recycle gas 106 and the product 107. On the other hand, the boiling liquid 108 which is a coolant is fed into the reactor 1 in which it is partly vaporized, and returned to the gas-liquid separator 110 for separation from the steam 109.

The test results according to the process using the reactor of the present invention are described.

Starting gas feed composition (mol%):

| | |
|---|---|
| CO | 7.5 |
| $CO_2$ | 7.3 |
| $H_2$ | 62.6 |
| $CH_4$ | 16.7 |
| $N_2$ | 5.6 |
| $H_2O$ | 0.0 |
| Methanol | 0.3 |

Gas composition at the outlet of reactor (mol%)

| | |
|---|---|
| CO | 2.8 |
| $CO_2$ | 6.7 |
| $H_2$ | 57.2 |
| $CH_4$ | 16.9 |
| $N_2$ | 6.5 |
| $H_2O$ | 1.9 |
| Methanol | 8.0 |

Space velocity of the starting gas feed: 12000 hr$^{-1}$
Temperature of boiling water for cooling: 250° C.
Reaction pressure: 100 kg/cm$^2$ Abs.

| | Test 1 | Test 2 | Test 3 |
|---|---|---|---|
| Inlet temperature of starting gas (A point) | 100° C. | 150° C. | 200° C. |
| Inlet temperature of catalyst bed (B point) | 230° C. | 240° C. | 250° C. |
| Maximum temperature at inlet portion (B' point) | 265° C. | 265° C. | 270° C. |
| Outlet temperature of catalyst bed (C point) | 245° C. | 250° C. | 255° C. |
| Amount of generated vapor per ton of methanol | 0.5 | 0.9 | 1.2 |

What is claimed is:

1. A process for exothermically reacting a starting fluid comprising hydrogen and carbon oxides and which is poor in methanol in a catalyst bed to form a product fluid which is rich in methanol and using an exothermic reactor having a coolant shell, an outer pipe spaced inwardly of said shell and defining a cooling space within said shell, said outer pipe having an upper open end and a lower open end, an inner pipe extending in said outer pipe and defining an annular space with said outer pipe, said inner pipe having an upper open end and a lower open end, sealing means enclosing and communicating with said lower open ends of said inner and outer pipes, a catalyst bed in said annular space between said inner and outer pipes, said catalyst bed being spaced upwardly from said sealing means and having an inlet at a lower end of said annular space, said catalyst bed having an outlet at an upper end of said annular space, a starting fluid inlet tube connected to said upper open end of said inner pipe, and a closing plate connected between said coolant shell and said outer pipe near said upper open end of said outer pipe, said closing plate defining an upper end of said coolant space, the process comprising supplying the starting fluid to said starting fluid inlet tube for passing downwardly through said inner pipe in a first direction and then into said inlet of said catalyst bed, said starting fluid passing upwardly in a second direction through said catalyst bed to form the product fluid in an exothermic reaction in said catalyst bed, supplying said product fluid out of said upper open end of said outer pipe and through said catalyst bed outlet above said closing plate, supplying boiling water as a coolant to a lower end of said coolant space through a coolant inlet in said coolant shell and at a location near said inlet of said catalyst bed and near said lower open ends of said inner and outer pipes, the coolant passing upwardly in said second direction through said coolant space, and removing coolant from said coolant space through a coolant outlet in said coolant shell at a location near an upper end of said coolant space and near said outlet of said catalyst bed, the starting fluid being exothermically reacted in the catalyst between the catalyst bed inlet and the catalyst bed outlet, part of the reaction heat being used as latent heat for evaporating said boiling water, employed as a coolant, the exothermic reaction having a characteristic minimum reaction rate line which is plotted on a graph relating the concentration of methanol to the temperature of the starting and product fluids during the reaction, the maximum reaction rate line having a high temperature at a low concentration for methanol and a low temperature at a high concentration of methanol, the process including supplying the starting fluid at a lower temperature than the lower temperature of the maximum reaction rate line, the starting fluid being heated as it moves along the inner pipe to the higher temperature of the maximum reaction rate line so as to cool the catalyst bed to form a temperature distribution along the inner pipe between the upper and lower temperatures of the maximum reaction rate line, the coolant cooling the catalyst bed between the catalyst bed inlet and the catalyst bed outlet, so as to maintain the temperature distribution along the catalyst bed.

2. A process for exothermically reacting a starting fluid comprising hydrogen and carbon oxides and which is poor in methanol and a catalyst bed to form a product fluid which is rich in methanol and using an exothermic reactor having a coolant shell, at least one outer pipe spaced inwardly of said shell defining a coolant space with said shell, said at least one outer pipe having an upper open end and a lower open end, an inner pipe extending in said at least one outer pipe and defining an annular space with said at least one outer pipe, said inner pipe having an upper open end and a lower open end, sealing means enclosing and communicating with said lower open ends of said inner and said at least one outer pipe, a catalyst bed in said annular space between said inner and at least one outer pipe, said catalyst bed being spaced upwardly from said sealing means and having an inlet at a lower end of said annular space, said catalyst bed having an inlet at an upper end of said annular space, a starting fluid outlet tube connected to said upper open end of said inner pipe, and a closing plate connected between said coolant shell and said at least one outer pipe near said upper open end of said at least one outer pipe, said closing plate defining an upper end of said coolant space, the process comprising: supplying the starting fluid to said starting fluid inlet tube for passing downwardly through said inner pipe in a first direction and then into said inlet of said catalyst bed; passing said starting fluid upwardly in a second direction through said catalyst bed to form the product fluid; exothermically reacting said starting fluid as the starting fluid passes through said catalyst bed to form the product fluid, the exothermic reaction having a characteristic maximum reaction rate, having a high temperature at a low concentration for methanol and a low temperature at a high concentration of methanol; supplying boiling water coolant to a lower end of said coolant space through a coolant inlet in said coolant shell, and at a location near said inlet of said catalyst bed and near said open ends of said inner and at least one outer pipe; passing said boiling water coolant upwardly in said second direction through said coolant space; using a portion of the reactor heat as latent heat for evaporating said boiling water coolant; removing said coolant from said coolant space through a coolant outlet in said coolant shell at a location near an upper end of said coolant space, and near said outlet of said catalyst bed; supplying said starting fluid at a lower temperature than the lower temperature associated with the maximum reaction rate; heating the starting fluid, as it moves along the inner pipe, to the higher temperature associated with the maximum reaction rate, so as to cool the catalyst bed to form a temperature distribution along the inner pipe between the lower and upper temperatures associated with the maximum reaction; cooling the catalyst bed between the catalyst bed inlet and the catalyst bed outlet, so as to maintain the temperature distribution along the catalyst bed.

* * * * *